United States Patent [19]

Chan et al.

[11] Patent Number: 4,931,080

[45] Date of Patent: Jun. 5, 1990

[54] SOLID, PHYTOACTIVE COMPOSITIONS, METHODS OF USE AND METHODS OF PREPARATION

[76] Inventors: Jimmy H. Chan, 5331 Alhambra Valley Rd., Martinez, Calif. 94553; Roger R. Djafar, One Seamast Passage, Corte Madera, Calif. 94925

[21] Appl. No.: 145,152

[22] Filed: Jan. 19, 1988

Related U.S. Application Data

[63] Continuation-in-part of Ser. No. 50,455, May 18, 1987, abandoned, which is a continuation of Ser. No. 762,466, Aug. 5, 1985, abandoned, which is a continuation-in-part of Ser. No. 738,708, May 29, 1985, abandoned.

[51] Int. Cl.$^5$ ............................................. A01N 25/00
[52] U.S. Cl. ........................................... 71/87; 71/86; 71/DIG. 1
[58] Field of Search ....................... 71/DIG. 1, 86, 87

[56] References Cited

U.S. PATENT DOCUMENTS 4,082,537  4/1987  Dudkowski .......................... 71/121
4,183,740  1/1980  Jang et al. .............................. 71/92
4,289,525  9/1981  Pasarela et al. ......................... 71/92

*Primary Examiner*—Glennon H. Hollrah
*Assistant Examiner*—Eric Jonathan Kraus
*Attorney, Agent, or Firm*—Denis A. Polyn

[57] ABSTRACT

Disclosed are solid, phytoactive, N-phosphonomethyl-N-carboxymethyl compositions. Also disclosed are processes for the preparation of such compositions by:

(a) forming an initial mixture comprising a phytoactive N-phosphonomethyl-N-carboxymethyl compound, a solvent and a molten surfactant, the surfactant being solid at ambient temperatures;

(b) removing solvent from the initial mixture to form a final mixture at a temperature above the melting point of the surfactant;

(c) cooling said final mixture to a temperature below the melting point of the surfactant to form a N-phosphonomethyl-N-carboxymethyl composition which is solid at ambient temperatures; and (d) processing said composition into particulate form, such as pellets, flakes, granules, or powders.

26 Claims, No Drawings

SOLID, PHYTOACTIVE COMPOSITIONS, METHODS OF USE AND METHODS OF PREPARATION

CROSS REFERENCE TO RELATED APPLICATIONS

This application is a continuation-in-part of application Ser. No. 050,455, filed May 18, 1987 now abandoned; which in turn is a continuation of application Ser. No. 762,466, filed August 5, 1985, now abandoned; which in turn is a continuation-in-part of application Ser. No. 738,708, filed May 29, 1985, now abandoned.

BACKGROUND OF THE INVENTION

This invention relates to novel, solid, phytoactive compositions comprising certain surfactants and phytoactive compounds containing the moiety:

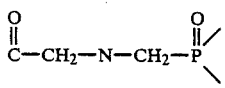

and to methods of manufacture of such compositions.

The phytoactive compounds containing the moiety set forth above as Formula I are designated herein as N-phosphonomethyl-N-carboxymethyl compounds or "PMCM" compounds. These compounds and the moiety of Formula I will be further defined and illustrated hereinafter. For convenience, the phytoactive compounds containing the moiety of Formula I will hereinafter be designated PMCM compounds.

THE PRIOR ART

A large number of phytoactive PMCM compounds are known in the art. The term "phytoactive" as used in describing this invention means effective as a plant growth regulator, as a herbicide, as a defoliant or the like. Illustrative of such PMCM compounds and their use are:

U.S. Pat. No. 3,455,675, Irani, July 15, 1969, entitled "Aminophosphonate Herbicides";

U.S. Pat. No. 3,556,762, Hamm, January 19, 1971, entitled "Increasing Carbohydrate Deposition in Plants with Aminophosphonates";

U.S. Pat. No. 4,405,531, Franz, September 20, 1983, entitled "Salts of N-Phosphonomethylglycine";

U.S. Pat. No. 3,868,407, Franz, February 25, 1975, entitled "Carboxyalkyl Esters of N-Phosphonomethylglycine;

U.S. Pat. No. 4,140,513, Prill, February 20, 1979, entitled "Sodium Sesquiglyphosate";

U.S. Pat. No. 4,315,765, Large, February 16, 1982, entitled "Trialkylsulfonium Salts of N-Phosphonomethylglycine;"

U.S. Pat. No. 4,481,026, Prisbylla, November 6, 1984, entitled "Aluminum N-Phosphonomethylglycine and Its Use As A Herbicide";

U.S. Pat. No. 4,397,676, Bakel, August 9, 1983, entitled "N-Phosphonomethylglycine Derivatives"; and International Application WO 84/03607, Chevron Research Company, September 27, 1984, entitled "Glyphosate-Type Herbicidal Compositions".

These patents are illustrative and are incorporated herein by reference. Most of these patents also include descriptions of processes employed to prepare such compounds. The following patents provide additional process descriptions.

U.S. Pat. No. 3,288,846, Irani et al., November 29, 1966, entitled "Process for Preparing Organic Phosphonic Acids";

U.S. Pat. No. 4,507,250, Bakel, March 26, 1985, entitled "Process for Producing N-Phosphonomethylglycine Acid";

U.S. Pat. No. 4,147,719, Franz, April 3, 1979, entitled "Process for Producing N-Phosphonomethylglycine"; and U.S. Pat. No. 4,487,724, Felix, December 11, 1984, entitled "Process for Preparation N-Phosphonomethylglycine Salts". These patents are also incorporated herein by reference.

PMCM compounds, in particular water soluble PMCM salts, are often difficult to obtain in a solid form. They can be difficult to crystallize and isolate from aqueous solutions. They can form glassy, non-crystalline solids which transform rapidly into wet cakes when exposed to the air.

Commercial formulations of PMCM compounds are generally not sold in a solid form, but sold as aqueous solutions. These solutions often contain only about 50% PMCM compound. Consequently, there is substantial waste in terms of storage, transportation charges and container disposal.

PMCM compounds in water are usually acidic and exhibit chelating properties. Iron and aluminum tend to inactivate the phytoactivity of the compounds. They can react with unlined or galvinized steel to produce hydrogen gas which can form a highly combustible gas mixture. If ignited, this mixture can flash or explode, which may cause serious personal injury. Therefore, aqueous solutions of the compounds are usually stored and transported in plastic or specially lined steel containers.

It would be desirable to package and sell PMCM compounds in a solid form in order to realize substantial savings in terms of storage, transportation and container disposal charges and to avoid the problems associated with PMCM solutions.

Representative patents generally disclosing wettable powders containing PMCM compounds include U.S. Pat. Nos. 4,025,331; 4,414,158; 4,481,026; and 4,405,531. They broadly disclose wettable powders containing a PMCM compound, an inert solid extender, and one or more surfactants. A disadvantage of such wettable powders is that the solid extender reduces the amount of active ingredients which can be transported in a container of a particular size. A further disadvantage is that many of the phytoactive compounds desirably contained in such powders, particularly PMCM salts, are hygroscopic or deliquescent. Great care is needed in packaging, storage and use of such wettable powders. If a final user chooses to employ only a portion of such a powder, extensive precautions must be taken to ensure the stability of the remainder.

SUMMARY OF THE INVENTION

It has now been found, however, that phytoactive PMCM compositions are readily obtained in a solid form which is substantially non-hygroscopic or non-deliquescent. Illustrative of a preferred process in accordance with the invention for preparing such solid compositions is the process of:

(a) forming an initial mixture comprising a phytoactive PMCM compound, a solvent and a molten surfactant, the surfactant being solid at ambient temperatures;

(b) removing solvent from the initial mixture at a temperature above the melting point of the surfactant to form a final mixture;

(c) cooling the final mixture to a temperature below the melting point of the surfactant to form an N-phosphonomethyl-N-carboxymethyl composition which is solid at ambient temperatures; and (d) processing said composition into particulate form, such as pellets, flakes, granules, or powders.

As used herein, the term "solid" refers to the physical state wherein the composition has a specific shape and volume and resists deformation. The solid may be processed into any suitable particulate form, such as pellets, flakes, granules, or powder. The solid composition can subsequently be dissolved in a suitable diluent, usually and preferably water, at a remote field site, and applied to the plants upon which the composition's phytoactivity is to be directed.

DETAILED DESCRIPTION OF THE PREFERRED EMBODIMENTS

Any liquid-dispersible, phytoactive PMCM compound can be used in the compositions and processes in accordance with the invention. The term "liquid-dispersible" is used in a broad sense to encompass compounds which are soluble in a liquid as well as compounds which are merely dispersible. In preferred embodiments, the PMCM compound is liquid-soluble. In most preferred embodiments, it is water-soluble.

The PMCM compounds may be represented by the formula

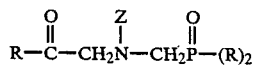

wherein Z is hydrogen, an organic moiety or an inorganic moiety. Representative patents disclosing PMCM compounds wherein Z is other than hydrogen include U.S. Pat. Nos. 3,888,915; 3,933,946; 4,062,699; 4,119,430; 4,322,239; and 4,084,953.

In preferred PMCM compounds, Z is hydrogen or an organic substituent. Representative organic substituents include methylene carboxylic; methylene phosphonic; methylene cyano; carbonyl, such as formyl, acetyl; benzoyl; perfluoroacyl; and thiocarbonyl; ethylene, such as cyano; carbamoyl or carboxyl substituted ethylene and benzene sulfonyl substitutents. Representative patents disclosing compounds wherein the nitrogen contains three organic substituents include U.S. Pat. Nos. 3,455,675; 3,556,762; 4,312,662; 4,216,727; 3,988,142; 3,970,695; 4,180,394; 4,047,927; 3,853,530; 4,203,756; 3,991,095; and 3,996,040. A preferred tertiary nitrogen substituted PMCM compound is N,N-bis-(phosphonomethyl)glycine. Those PMCM compounds wherein Z is hydrogen are most preferred when the phytoactivity desired is herbicidal activity.

Representative R's include halogen, —NHOH, —N($R^1$)$_2$, —O$R^2$, —S$R^3$ and OM, where $R^1$ is independently selected from hydrogen; alkyl or hydroxyalkyl, preferably containing less than about 5 carbon atoms; alkenyl, preferably containing less than about 5 carbon atoms; or phenyl moieties. $R^1$ is independently selected from hydrogen; alkyl; hydroxyalkyl; or chloroalkyl, preferably containing less than about 5 carbon atoms; alkoxy, preferably containing less than about 5 carbon atoms; alkyleneamine, preferably containing less than about 12 carbon atoms; phenyl; or benzyl moieties.

M is selected from hydrogen and agriculturally acceptable salt-forming moieties such as alkali metal, alkaline earth metal, stannic, ammonium, organic ammonium, alkylsulfonium, alkylsulfoxonium, alkylphosphonium moieties or combinatins thereof. Representative patents disclosing at least some of such compounds include U.S. Pat. Nos. 3,799,758; 4,397,676; 4,140,513; 4,315,765; 3,868,407; 4,405,531; 4,481,026; 4,414,158; 4,120,689; 4,472,189; 4,341,549; and 3,948,975.

The above patents are herein incorporated by reference.

Illustrative of agriculturally acceptable salt-forming moieties represented by M are the alkali metals having atomic weight of from 22 through 133, inclusive, such as sodium, potassium or rubidium; the alkaline earth metals having atomic weights of from about 24 through 88, inclusive, such as magnesium or calcium; ammonium and aliphatic ammonium, wherein the aliphatic ammonium is primary, secondary, tertiary or quaternary and preferably wherein the total number of carbon atoms does not exceed more than about 12; phenylammonium; tiralkylsulfonium; preferably wherein the total number of carbons in the three alkyl substituents does not exceed more than about 6, such as trimethylsulfonium, ethyldimethylsulfonium, propyldimethylsulfonium and the like; trialkylsulfoxonium, preferably wherein the total number of carbon atoms in the three alkyl substituents does not exceed more than about 6, such as trimethylsulfoxonium, ethyldimethylsulfoxonium, propyldimethylsulfoxonium and the like; tetraalkylphosphonium, ethyltrimethylphosphonium, propyltrimethylphosphonium and the like.

It should be noted that the alkaline earth metal salts, while agriculturally acceptable, provide only marginal herbicidal activity.

In preferred compositions according to this invention, M is independently selected from the above-described agriculturally acceptable salt-forming moieties and hydrogen. In more preferred compositions, M is an alkali metal, ammonium, monoalkylammonium, or trialkylsulfonium moiety. In most preferred compositions only one M is an alkali metal, ammonium, monoalkyl ammonium, or trialkylsulfonium moiety, while the other two M's are hydrogen. Representative most preferred compositions include isopropylamine N-phosphonomethylglycyine, trimethylsulfonium N-phosphonomethylglycine and sodium sesqui-N-phosphonomethylglycine. Combinations of two or more PMCM compounds can be employed in the compositions and processes in accordance with the invention.

The choice of the particular surfactant to be used with a PMCM compound is important. The choice of a particular surfactant to be used in connection with a particular PMCM compound will be easily made by one skilled in the art, without undue experimentation based on the teachings of this application. Whatever surfactant is used, it must be a solid at ambient temperature, i.e., it must have a high melting point. Preferred surfactants have a melting point above 50° C. The surfactant should also not be hygroscopic or deliquescent. When solid, the surfactant should be readily soluble or dispersible in the diluent chosen by the ultimate user of the phytoactive composition. In preferred embodiments, the solid surfactante is soluble in water. The surfactant should cause a minimum amount of foaming, particularly under vacuum, when the solvent is removed during the processes in accordance with the invention and should case a minimum amount of foaming when the final product is subsequently mixed with the diluent.

It is particularly important that the surfactant is solid at ambient temperatures. In practical terms, it must be solid at the highest temperatures to which the solid product may be exposed before it is mixed with the diluent by the ultimate user. Such temperatures are generally in the range of from about −20° C. to 50° C.

Preferred surfactants for use in the invention are nonionic block copolymers of alkyl oxides having a functional group

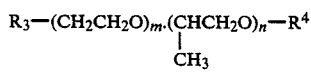

wherein $R^3$ and $R^4$ are the same or different and are selected from hydrogen,

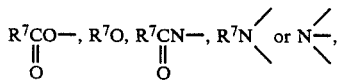

and wherein $R^7$ is selected from an alkyl having from about 8 to about 30 carbon atoms or an alkylaryl group, wherein the alkyl portion of the alkylaryl group ranges from about 8 to about 30 carbon atoms, and mixtures thereof, and wherein m ranges from about 20 to about 200, n ranges from about 0 to about 10, and m+n is equal to or greater than about 25.

Examples of $R^7$ include sorbitan, fatty radicals such as coco, oleyl, palmityl, tallow, stearyl, lauryl, soya, castor, nonylphenoxy, dinonylphenoxy, octylphenoxy, and dioctylphenoxy.

Preferred nonionic surfactants for use in the compositions of the invention include Pluronic surfactants, such as Pluronic F-38, F-68, F-77, F-87, F-88, F-89, F-108 and F-127. The Pluronic surfactants are available commercially (BASF), and comprise ethylene oxide or propylene oxide block copolymers.

The advantages of the use of a nonionic surfactant in the process and compositions of this invention are that they are generally inexpensive, readily available, low or non-irritating, often of low toxicity mammals and generally, low or non-foaming when under vacuum in a molten state.

Other surfactants can be used, such as cationic, anonic, or amphoteric surfactants. However, they may give rise to foaming. They also may be more toxic to mammals.

Such other surfactants include Emcol CC-57 (cationic), Arquad C-50 (cationic), Ethomeen 18/12 (cationic), Ethomeen 18/14 (cationic), Ethomeen 18/60 (cationic), Ethomeen T/60 (cationic), Alkaphos K-380 (anionic) and Witconate AOK (anionic).

Mixtures of various nonionic surfactants, or nonionics with cationic, anionic or amphoteric surfactants, can also be used if desired.

The following surfactants, among others, have been found to be useful in the processes and compositions of this invention.

TABLE II

| Surfactant | Manufacturer | Structure/Type | m.p. °C. |
|---|---|---|---|
| Trycol 5946 | Emery | tridecyl alcohol EO* | 39 |
| Trycol 59t7 | Emery | lauryl alcohol EO | — |
| Trycol 5964 | Emery | lauryl alcohol EO | 39 |
| Trycol 6954 | Emery | nonylphenol 15 EO | — |
| Trycol NP-20 | Emery | nonylphenol 20 EO | 34 |
| Trycol LAL-12 | Emery | lauryl alcohol 12 EO | 32 |
| Trycol LAL-23 | Emery | lauryl alcohol 23 EO | 40 |
| Trycol OAL-23 | Emery | alkyl alcohol 23 EO | 47 |
| Emery 6873 | Emery | — | — |
| Trycol 6988 | Emery | dinonylphenol 15 EO | 55 |
| Pluronic F-88 | BASF | block EO, PO** copolymer | 54 |
| Industrol MS-40 | BASF | polyethylene glycol fatty acid esters 40 EO | 48 |
| Iconol DNP-150 | BASF | dinonylphenol 15 EO | 55 |
| Pluronic F-127 | BASF | block EO, PO copolymer | 56 |
| Pluronic F-108 | BASF | block EO, PO copolymer | 56 |
| Plurafac A-39 | BASF | linear alcohol ethoxylate | 56 |
| Alkasurf S-40 | Alkaril | stearic acid ethoxylate 40 EO | 46 |
| Alkasurf TA-50 | Alkaril | tallow alcohol ethoxylate 50 EO | 47 |
| Alkasurf OP-40 | Alkaril | octylphenol ethoxyate 40 EO | 48 |
| Alkasurf LAD-23 | Alkaril | fatty alcohol ethoxylate 23 EO | 47 |
| Alkatronic PGP-18-8 | Alkaril | block EO, PO copolymer (80% EO) | 52 |
| Alkatronic PGP-23-8 | Alkaril | block EO, PO copolymer (80% EO) | — |
| Alkatronic PGP-33-8 | Alkaril | block EO, PO copolymer (80% EO) | 57 |
| T-DET BP-1 | Thompson-Hayward | | 28 |
| T-DET N-100 | Thompson-Hayward | nonylphenol 100 M EO | 50 |
| Staley APG 91-3 (solid form) | A. E. Staley | alkyl polyglyoside | |

*EO = ethylene oxide
**PO = propylene oxide

Additional classes of surfactants which can be used in accordance with the invention are listed in Table II below.

TABLE III

| Surfactants | Type | Structure |
|---|---|---|
| Alkamuls Industrol Alkasurf Trydet | fatty acid ethoxylate | $RCO(CH_2CH_2O)_xCH_2CH_2OH$ |
| Aklamuls Industrol Emerest | di-fatty acid esters | $RCOCH_2CH_2O(CH_2CH_2O)_xCH_2CH_2OCR$ |
| Alkamuls Emsorb | sorbitan ester ethoxylate | 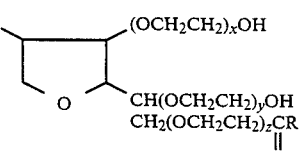 |

TABLE III-continued

| Surfactants | Type | Structure |
| --- | --- | --- |
| Alkaminox Trymeen | amine ethoxylate | $RN\begin{cases}(CH_2CH_2O)_xCH_2CH_2OH \\ (CH_2CH_2O)_yCH_2CH_2OH\end{cases}$ |
| Alkasurf Industrol | castor oil ethoxylates | $\begin{array}{c}O(CH_2CH_2O)_xCH_2CH_2OH \\ | \\ CH_3(CH_2)_5CHCH_2CH=CH(CH_2)_7\overset{O}{\underset{\|}{C}}OCH_2 \\ | \\ RO-CH \\ | \\ RO-CH_2\end{array}$ |
| Pluronic | polyoxypropylene glycol ethoxylate | $HO(CH_2CH_2O)_x-(CHCH_2O)_y-(CH_2CH_2O)_2-H$ <br> $\phantom{HO(CH_2CH_2O)_x-(}CH_3$ |
| Alkamidox Emid | alkanolamide ethoxylates | $\overset{O}{\underset{\|}{RCN}}\begin{cases}(CH_2CH_2O)_xH \\ (CH_2CH_2O)_yH\end{cases}$ |
| Alkasurf Industrol Plurafac Iconol Trycol | alcohol ethoxylates | $R-(OCH_2CH_2)_x-OH$ |

Some surfactants which are solid at ambient temperatures foam. The foaming problem may arise both during the initial preparation of the composition, particularly if the solvent is removed under vacuum, and when the final product is subsequently mixed with a diluent by the ultimate user. Therefore, some embodiments of the invention include an anti-foaming agent. The anti-foaming agent may be added any time before the solvent is removed.

Representatives of useful anti-foaming agents include compounds such as Silcolapse 5008 (silicone-based anti-foam) and Anti-foam Emulsion Q-94 (SWS Silicones Corp.).

In addition to the PMCM compound, the surfactant and the anti-foaming agents, the composition can also include other conventional adjuvants such as drying aids, heat stabilizers, ultraviolet absorbers, dispersants, wetting agents, and other agriculturally acceptable materials. Representative drying aids include Microcel E, Aerosil 200, and Hi-Sil® 233. Representative heat stabilizers include phenylenediamines, phenazine, butylated hydroxy toluene. Representative ultraviolet adsorbers include Tinuvin 770, Tinuvin P and dinitroanilines.

The ratio of PMCM compound to surfactant varies over a wide range. Since it is known hat the choice of a particular surfactant can affect the phytoactivity of the PMCM compounds used in accordance with this invention, the desired activity of the solid composition should be considered when selecting a particular surfactant. As much surfactant as desired may be employed so long as the products dissolve totally or disperse readily in the diluent prior to the application. For cost considerations, a minimum of surfactant should be used which still enables the objects of the invention to be obtained, e.g., the production of a solid product which is substantially non-hygroscopic. The ratio of PMCM compound to surfactants by weight is typically from about 10:1 to about 1:10. The preferred ratio is from about 4:1 to about 1:2. The most preferred is from about 2:1 to about 1:1.

Representative formulations of the compositions of this invention are as follows. The formulations are based on percent by weight, unless otherwise noted.

| | |
| --- | --- |
| 69.3% | trimethylsulfonium salt of N-phosphonomethylglycine |
| 30.7% | F-108 *m.p. 57° C.) |
| 100.0% | Total |
| 69.3% | isopropylamine salt of N-phosphonomethylglycine |
| 30.7% | Tetronic 909 (m.p. 59° C.) |
| 100.0% | Total |
| 69.3% | isopropylamine salt of N-phosphonomethylglycine |
| 30.7% | Pluronic F-108 (m.p. 57° C.) |
| 100.0% | Total |

The solid compositions in accordance with this invention are characterized in that the PMCM compound forms an antimate mixture with the surfactant. The PMCM compound is initially dispersed throughout a surfactant matrix. It is believed that such an intimate dispersion prevents absorption of moisture by the PMCM compounds.

The compositions of this invention can be prepared in any suitable manner. A preferred process, however, comprises first preparing a mixture containing the PMCM compound and the solvent. In preferred embodiments, the PMCM compound is dissolved in the solvent. In other embodiments, the PMCM compound is dispersed therein.

In some embodiments, the mixture is prepared by forming the PMCM compound in situ. For example, in some embodiments, N-phosphonomethylglycine is reacted with a desired base, in the presence of water, to form an aqueous solution containing the PMCM compound. In preferred embodiments, solutions of isopropylamine N-phosphonomethylglycine can be prepared in this manner.

The choice of the solvent for use in accordance with the process of the invention is not critical, but the solvent must meet certain requirements. The solvent must be capable of dissolving or dispersing a desired PMCM compound at the temperature used to form the initial mixture, without adversely effecting the PMCM compound's phytoactivity. The greater the solubility or ease or dispersibility of the PMCM compound in solvent, the less solvent will be required and the subsquent removal of solvent will be facilitated.

It is preferred that the normal boiling point of the solvent is greater than the melting of the particular surfactant chosen. However, what is most important is that the solvent be removed at a temperature greater than the surfactant's melting point. Consequently, where the normal boiling point of the solvent is less than the melting point of the surfactant, the solvent must be removed under elevated pressure. Preferred solvents include water and polar organic solvents, such as methanol, ethanol, isopropyl alcohol and acetone. Water is most preferred.

The third component of the initial mixture is the surfactant. The surfactant may be added by conventional techniques to the solvent before, during or after the addition of the PMCM compound. Preferably, the surfactant is added in the molten state, although in some embodiments it is initially merely dissolved or dispersed in the solvent and the temperature then raised above the melting point of the surfactant. Initial use of a molten surfactant permits easy mixing and can aid in reducing the amount of solvent, which is required. In those embodiments where the molten surfactant is itself capable of dissolving or dispersing the desired PMCM compound, it can be employed in lieu of the solvent.

In order to form or maintain the molten surfactant, the lower limit on the temperature of the initial mixture is the melting point of the surfactant. The upper limit is the temperature at which a particular PMCM compound, surfactant or other additives will decompose. When trialkylsulfonium-N-phosphonomethylglycines are chosen as a PMCM compound, temperatures in the range of 30° to 110° C. are generally employed.

The solvent is then removed from the initial mixture. Any solvent removal technique can be employed, so long as the temperature is below the decomposition temperature of and is above the melting point of the surfactant. Representative techniques include heating and vacuum techniques and combinations of both. For example, the final mixture can simply be heated to a temperature sufficient to evaporate the solvent of the above requirements are met.

The temperature at which the solvent is evaporated is a function of temperature, absolute pressure and composition of the mixture. Thus, if a reduced pressure is employed, removal of the solvent can be achieved at lower temperatures. A preferred device for solvent removal at reduced pressure is an industria-type film evaporator. Because the residence time of the product in the device is very short, any decomposition which may tend to occur is minimized.

In carrying out the process of this invention, atmospheric conditions are most preferred for solvent removal because they eliminate the use of special equipment, or special techniques for maintaining a vacuum and for removing the resulting solid composition from such equipment.

As the solvent is removed at temperatures above the melting point of the surfactant and higher concentrations of surfactant are contained in the mixture, a viscous final mixture is formed. Upon cooling, the final mixture readily solidifies. It is not necessary to remove all the solvent from the final mixture. All that is required is that sufficient solvent be removed so that the final composition solidifies upon cooling. In preferred embodiments, however, substantially all the solvent is removed.

The resulting solid composition can then be processed into any suitable particulate form, such as pellets, flakes, granules, or powder, by conventional techniques. As will be readily appreciated by one skilled in the art, the size of the final particle will affect the ease of solution or dispersion of the final product in the diluent by the ultimate user. Generally, the ease of solution or dispersion increases as particle size decreases. In contrast, however, the ease of handling the final product increases as particle size increases. The more soluble or dispersible the solid composition, the larger the particle size than can be employed. In preferred embodiments, the final product is processed into particles ranging from powders having a diameter of about 3 to about 15 microns, to granules having a diameter of about 8 to about 30 mesh to flakes.

The following examples illustrate production of the compositions of the invention in accordance with the process described herein. All percentages are based on weight, unless otherwise clearly indicated.

EXAMPLE 1

In a laboratory Buchi Rotavapor, 12.5 grams (g) of TETRONIC® 908 surfactant (block copolymer of ethylene oxide and propylene oxide from BASF), m.p. 58° C., were melted in a 200 milliliter (ml) round-bottom flask at 70° C. To the molten surfactant 42.5 g of a 58% aqueous trimethylsulfonium-N-phosphonomethylglycine solution at ambient temperature were added slowly while the elevated temperature was maintained. The mixture was heated slowly to 95° C. under vacuum (5 mmHg absolute pressure) and moderately rotated to control ebullition. After ½ hour, substantially all the water had been removed and the mixture was solidified by cooling to room temperature. The solids obtained were removed from the flask with a spatula and ground into a powder with a pestle and a mortar under nitrogen. A sample of the powder left in an open crucible did not deliquesce.

EXAMPLE 2

A composition was prepared as in Example I, except for using 12.5 g of IGEPAL DM 970 (dialkylphenoxypol(ethylenoxy)ethanol from GAF Corp.) as the surfactant. A solid was obtained which did not deliquesce upon standing in the open.

EXAMPLE 3

A composition was prepared as in Example 1, except for using 15 g of ICONOL DNP 150, m.p. 55° C., as the surfactant, 1 g of Hi-Sil® (fumed silica from PPG), 2 drops of anti-foaming agent (Silcolapse 5008) and evaporating at 100° C. for one-half hour at 1 mmHg (absolute). A solid was obtained which did not deliquesce upon standing in the open.

EXAMPLE 4

A composition was prepared as in Example 1, except for using 15 g of PLURONIC® F-108, m.p. 56° C., as the surfactant and evaporating at 95° C. for ½ hour at 10 mmHg. The viscous paste obtained was solidified by cooling to room temperature. It did not deliquesce upon standing in the open.

EXAMPLE 5

A composition was prepared as in Example 4, except for using a mixture of 2 surfactants (10 g of PLURONIC ® 17R8 and 5 g of TRYCOL ® 5946, ethoxylated alkylphenol surfactant from Emery) and evaporating at 5 mmHg absolute pressure (final condition) and 100° C. for 15 minutes. The viscous paste obtained solidified after cooling to room temperature. It did not deliquesce upon standing in the open.

EXAMPLE 6

A composition was prepared as in Example 1, except for using 15 g of PLURONIC ® F-108, m.p. 56° C., 1 g of Hi-Sil ® (fumed silica from PPG) and evaporating at 5 mmHg absolute pressure (final condition) at 100° C. for ½ hour. The product obtained solidified quickly when cooled. It did not deliquesce upon standing in the open.

EXAMPLE 7

A composition was prepared as in Example 1, except for using 25 g of PLURAFAC A-39 (a linear alcohol ethoxylate surfactant from BASF), m.p. 56° C., as the surfactant and evaporating at 1 mmHg absolute pressure (final condition) at 100° C. for ½ hour. The viscous liquid obtained solidified when cooled to room temperature. It did not deliquesce upon standing in the open.

EXAMPLE 8

In a laboratory Buchi Rotavapor, 12.5 g of IGEPAL ® DM 970 surfactant [trialkylphenoxy poly(ethyleneoxy)ethanol from GAF Corp.] were melted in a 200 ml round-bottom flask at 70° C. To the molten surfactant, 47.8 g of a 53.5 wt. % isopropylamino-N-phsophonomethylglycine aqueous solution (Rodeo from Monsanto) at ambient temperature was maintained. The mixture was then heated slowly to 95° C. under vacuum (5 mmHg absolute pressure) and moderately rotated to control the ebullition. After ½ hour substantially all the water had been removed and the mixture was cooled to room temperature. The solids obtained were removed from the flask with a spatula and ground into a powder with a pestle and a mortar under nitrogen. A sample of the powder left in an open crucible did not deliquesce.

EXAMPLE 9

A composition was prepared as in Example 8, except for using 12.5 g of PLURONIC 17R8 surfactant (block copolymer of propylene oxide and ethylene oxide from BASF, Wyandotte) and evaporating at 90° C. for ½ hour at 5 mmHg (absolute). The resulting solid product did not deliquesce.

EXAMPLE 10

Twelve additional powders were prepared. All the solids obtained were ground into water-soluble powders. The powders were prepared as follows:

(a) Six different surfactants (15 g for each powder) were mixed with 1 g of Hi-Sil ® (fumed silica from PPG) and 42.5 g of a 58% aqueous solution of trimethylsulfonium-N-phosphonomethylglycine and worked-up as in Example 6. Table III indicates the surfactants used.

TABLE III

| Powder | Tradename | Mfgr. | Surfactants Melting point (°C.) | Average Molecular Weight | Viscosity @ 77° C. (cps) | Class or Formula |
|---|---|---|---|---|---|---|
| 1 | Pluronic ® 108 | BASF | 57 | 14,600 | 2800 | Polyol |
| 2 | Tetronic ® 909 | BASF | 59 | 30,000 | 8200 | Polyol |
| 3 | Pluracol ® E8000 | BASF | 61 | 7,500 | — | Polyethylene glycol |
| 4 | Plurafac ® A-39 | BASF | 56 | 2,600 | 125 | Linear alcohol ethoxylate |
| 5 | Iconol ® DNP-150 | BASF | 55 | 6,900 | — | Dinonylphenol ethoxylate |
| 6 | Trycol ® 6954 | Emery | 54 | — | — | Nonylphenol ethoxylate |

(b) In addition, six powders were prepared from a combination of two surfactants, Iconol DNP-150, m.p. 55° C. and Trycol ® 6954, m.p. 54° C., at 3 different levels: 15, 20 and 25 g with 42.5 g of a 58 wt. % solution of trimethylsulfonium-N-phosphonomethylglycine as in Example 6. In each instance a dry powder was obtained.

EXAMPLE 11

A composition was prepared as in Example 1, except for using 300 g of Pluronic F-88 (block copolymer of propylene oxide) and ethylene oxide (from BASF, m.p. 54° C.) as the surfactant, 574 g of a 58% aqueous trimethylsulfonium-N-phosphonomethylglycine solution, 10 drops of Silcolapse 5008 and mixing in a 2 liter round-bottomed flask. The solid obtained did not deliquesce upon standing in the open.

The phytoactive compositions of this invention are effective when subsequently dissolved or dispersed in a suitable diluent, preferably water, and applied to the locus desired by spray or other conventional means. Conventional adjuvants, including wetting agents, penetrating agents, spreading or sticking agents, carriers, extenders and conditioning agents, such as dispersing agents can be added to the final solution or dispersion.

The following examples demonstrate the herbicidal effectiveness of the compositions of the invention. The effectiveness was observed by comparing the extent of weed control in test containers treated with the PMCM compositions in accordance with the invention with that occurring in similar control containers. The soil used in these tests was a sandy loam soil from the Livermore, California area.

The soil was treated by the addition of 17-17-17 fertilizer ($N-P_2O_5-K_2O$ on a weight basis), amounting to 50 ppm by weight, with respect to the soil, and CAPTAN ®, a soil fungicide.

The thus treated soil was then placed in plastic tubs, 6 inches in diameter and 5 inches deep with drainage holes. Johnsongrass rhizomes, Bermuda grass cuttings and purple nutsedge tubers were planted in the test containers. The test weeds were as follows: Johnsongrass (*Sorghym halepense*), Bermuda grass (*Cynodon dactylon*) and purple nutsedge (*Cyperus rotundus*).

Sufficient stock or cuttings were planted to produce several seedlings per container. After planting, the containers were placed in a greenhouse maintained at 21° to 30° C. and watered daily with a sprinkler.

A variety of PMCM compositions based on trimethylsulfonium-N-phosphonomethylglycine were sprayed on the seedling approximately 35 days after planting. The compositions are shown in Table IV. Composition 1 was a liquid formulation. Compositions 2 through 13 were solid compositions, produced in accordance with the invention. Each composition was dissolved in 400 ml of water and then a 40 ml aliquot of the resulting solution was used for spraying at the rates indicated in Table IV.

Approximately 28 days after the spraying, the degree of weed control was rated and recorded as a percentage control compared to the control exhibited on the same species of the same age which had not been sprayed. The rating ranged from 0 to 100%, were 0 equals no effect on plant growth when compared to the untreated control, and 100 equals complete killing of the test weeds.

The results are listed in Table IV.

TABLE IV

| Composition | Weight in grams | Rate (lb/A) | Percent Control Ratings | | |
|---|---|---|---|---|---|
| | | | Johnson grass | Bermuda grass | Purple Nutsedge |
| 1. Herbicide | 3.84 | ¼ | 65 | 65 | — |
| Ethoquad 12 | 1.54 | ½ | 97 | 99 | 55 |
| | | 1 | — | — | 93 |
| 2. Herbicide | 3.84 | ¼ | 40 | 15 | — |
| Pluronic F-108 | 2.30 | ½ | 85 | 55 | 45 |
| | | 1 | — | — | 93 |
| 3. Herbicide | 3.84 | ¼ | 25 | 10 | — |
| Tetronic 909 | 2.30 | ½ | 80 | 45 | 40 |
| | | 1 | — | — | 85 |
| 4. Herbicide | 3.84 | ¼ | 10 | 15 | — |
| Pluracol E 8000 | 2.30 | ½ | 75 | 50 | 35 |
| | | 1 | — | — | 80 |
| 5. Herbicide | 3.84 | ¼ | 15 | 25 | — |
| Plurafac A-39 | 2.30 | ½ | 80 | 60 | 25 |
| 6. Herbicide | 3.84 | ¼ | 15 | 15 | — |
| Iconol DNP-150 | 2.30 | ½ | 70 | 60 | 25 |
| | | 1 | — | — | 75 |
| 7. Herbicide | 3.84 | ¼ | 35 | 20 | — |
| Trycol 6954 | 2.30 | ½ | 80 | 70 | 25 |
| 8. Herbicide | 3.84 | ¼ | 35 | 20 | — |
| Iconol DNP-150 | 2.68 | ½ | 75 | 70 | 35 |
| | | 1 | — | — | 85 |
| 9. Herbicide | 3.84 | ¼ | 25 | 35 | — |
| Iconol DNP-150 | 3.07 | ½ | 75 | 70 | 45 |
| | | 1 | — | — | 80 |
| 10. Herbicide | 3.84 | ¼ | 25 | 35 | — |
| Iconol DNP-150 | 3.84 | ½ | 75 | 70 | 50 |
| | | 1 | — | — | 80 |
| 11. Herbicide | 3.84 | ¼ | 35 | 35 | — |
| Iconol DNP-150 | 3.84 | ½ | 85 | 80 | 35 |
| | | 1 | — | — | 75 |
| 12. Herbicide | 3.84 | ¼ | 40 | 35 | — |
| Plurafac A-39 | 3.07 | ½ | 85 | 75 | 35 |
| | | 1 | — | — | 88 |
| 13. Herbicide | 3.84 | ¼ | 55 | 40 | — |
| Plurafac A = 39 | 3.84 | ½ | 95 | 98 | 35 |
| | | 1 | — | — | 93 |
| Control | | 0 | 0 | 0 | 0 |
| | | 0 | 0 | 0 | 0 |

EXAMPLE 12

Another series of formulations was prepared in accordance with the general technique set forth in Example 1. The active herbicide ingredient was mixed with a melted surfactant, then the mixture was cooled below the solidification temperature of the surfactant to form the formulation wherein the active herbicide particles were enmeshed in the surfactant matrix. This enabled a non-hygroscopic formulation to be prepared.

The formulation were as follows:

| 1. N-phosphonomethylglycine acid | 51.90% | (48.2 a.i.) |
|---|---|---|
| Pluronic F-108 | 48.10% | |
| | 100.0% | |
| 2. isopropylamine salt of N-phosphonomethylglycine | 52.10% | (48.1 a.i.) |
| Pluronic F-108 | 47.90% | |
| | 100.00% | |
| 3. sodium salt of N-phosphonomethylglycine | 59.80% | (51.6 a.i.) |
| Pluronic F-108 | 40.20% | |
| | 100.00% | |
| 4. ammonium salt of N-phosphonomethylglycine | 52.80% | (50.2 a.i.) |
| Pluronic F-108 | 47.20% | |
| | 100.00% | |
| 5. magnesium salt of N-phosphonomethylglycine | 64.20% | (51.4 a.i.) |
| Pluronic F-108 | 35.80% | |
| | 100.00% | | a.i. = active ingredient

Each of these formulations was tested for herbicidal activity in accordance with the general procedure set forth above regarding the previous herbicide tests.

The following quantities of each formulation were measured into a beaker and sufficient water was added to achieve a volume of 40 milliliters (ml).

| Formulation 1 | 0.797 grams |
|---|---|
| Formulation 2 | 0.793 grams |
| Formulation 3 | 0.744 grams |
| Formulation 4 | 0.765 grams |
| Formulation 5 | 0.747 grams |

To achieve the desired application rates, each formulation was diluted with water in the following manner.

¼ lb/A=5 ml+35 ml water (total 40 ml)

½ lb/A=10 ml+30 ml water (total 40 ml)

1 lb/A=20 ml+20 ml water (total 40 ml)

The soil used in these tests was a sandy loam soil from the Keeton, California area.

The soil was treated by the addition of 17-17-17 fertilizer (N—P$_2$O$_5$—K$_2$O on a weight basis), amounting to 50 ppm by weight, with respect to the soil, and CAPTAN ®, a soil fungicide.

The thus treated soil was then placed in plastic tubs, 6 inches in diameter and 5 inches deep with drainage holes. Johnsongrass and quackgrass rhizomes, Bermuda grass cuttings and purple nutsedge tubers were planted in the test containers. The tests weeds were as follows: Johnsongrass (*Sorghum halepense*), Bermuda grass (*Cynodon dactylon*), purple nutsedge (*Cyperus rotundus*) and quackgrass (*Agropyron repens*).

Sufficient stock or cuttings were planted to produce several weed plants per container. After planting, the containers were placed in a greenhouse maintained at 21° to 31° C. and watered daily with a sprinkler.

The formulations of N-phosphonomethylglycine were sprayed on the weed approximately 35 days after planting.

A 40 ml aliquot of each composition, prepared in accordance with the method set forth above, was applied post-emergence to the weed species utilizing a linear spray table at 25 gal/A using a 80015 nozzle set at 40 psi.

Approximately 32 days after the spraying, the degree of weed control was rated and recorded as a percentage control compared to the control exhibited on the same species of the same age which had not been sprayed. The rating ranged from 0 to 100%, where 0 equaled no effect on plant growth when compared to the untreated control, and 100 equals complete killing of the test weeds.

The results of these tests are listed in Table V.

TABLE V

| Treatment | Rate (lb/A) | Johnson-grass | Bermuda-grass | Quack-grass | Purple Nutsedge |
|---|---|---|---|---|---|
| Formulation #1 | 0.25 | 80 | 55 | 35 | — |
|  | 0.5 | 100 | 85 | 93 | 40 |
|  | 1.0 | — | — | — | 98 |
| Formulation #2 | 0.25 | 80 | 50 | 40 | — |
|  | 0.5 | 100 | 80 | 85 | 40 |
|  | 1.0 | — | — | — | 85 |
| Formulation #3 | 0.25 | 80 | 30 | 35 | — |
|  | 0.5 | 100 | 75 | 80 | 35 |
|  | 1.0 | — | — | — | 85 |
| Formulation #4 | 0.25 | 80 | 35 | 50 | — |
|  | 0.5 | 100 | 80 | 75 | 40 |
|  | 1.0 | — | — | — | 80 |
| Formulation #5 | 0.25 | 20 | 10 | 25 | — |
|  | 0.5 | 70 | 45 | 60 | 20 |
|  | 1.0 | — | — | — | 50 |
| Control |  | 0 | 0 | 0 | 0 |

(—) indicates not tested.

The amount of the composition which constitutes a phytoactive amount depends on the nature of the plants and the effect desired. The rate of application generally varies from about 0.01 to about 50 pounds of PMCM compound per acre, preferably about 0.1 to about 25 pounds per acre with the actual amount depending on the overall cost and the desired results. It will be readily apparent to one skilled in the art that compositions exhibiting lower phytoactivity will require a higher application rate than the more active compounds for the same degree of effectiveness.

What is claimed is:

1. A solid, substantially non-hygroscopic, phutoactive composition comprising an intimate mixture of a phytoactive N-phosphonomethyl-N-carboxymethyl compound and a surfactant, where the surfactant is solid at ambient temperature and said phytoactive N-phosphonomethyl-N-carboxymethyl compound is dispersed throughout a matrix formed by said surfactant.

2. A compoistion according to claim 1 wherein the N-phosphonomethyl-N-carboxymethyl compound is of the formula

and where M is independently selected from hydrogen and agriculturally acceptable salt-forming moieties.

3. A composition according to claim 2 wherein one M is selected from an agriculturally acceptable salt-forming moiety and the remaining M's are hydrogen.

4. A composition according to claim 1 wherein the N-phosphonomethyl-N-carboxymethyl compound is N,N-bis-(phosphonomethyl)glycine.

5. A composition according to claim 2 wherein the N-phosphonomethyl-N-carboxymethyl compound is N-phosphonomethylglycine.

6. A composition according to claim 3 wherein the N-phosphonomethyl-N-carboxymethyl compound is isopropylamine-N-phosphonomethylglycine.

7. A composition according to claim 3 wherein the N-phosphonomethyl-N-carboxymethyl compound is trimethylsulfonium-N-phosphonomethylglycine.

8. A composition according to claims 1, 2, 3, 4, 5, 6 or 7 wherein the surfactant is nonionic.

9. A composition according to claims 1, 2, 3, 4, 5, 6 or 7 wherein the surfactant is an ethylene oxide or propylene oxide block copolymer.

10. A composition according to claims 1, 2, 3, 4, 5, 6 or 7 wherein the surfactant is a block copolymer of alkyl oxides having a functional group

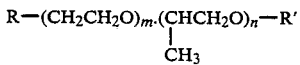

wherein R and R' are independently selected from hydrogen,

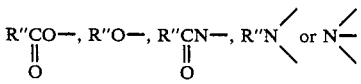

wherein R" is selected from an alkyl group having from about 8 to about 30 carbon atoms or alkylaryl groups, wherein the alkyl portion of the alkylaryl group ranges from about 8 to about 30 carbon atoms, and mixtures thereof, and wherein m ranges from about 20 to about 200, n ranges from about 0 to about 10, and m+n is equal to or greater than about 25.

11. A method for the preparation of a solid, phytoactive composition comprising:
(a) forming an initial mixture comprising a phytoactive N-phosphonomethyl-N-carboxymethyl compound, a solvent and a molten surfactant, the surfactant being solid at ambient temperatures;
(b) removing solvent from said initial mixture to form a final mixture at a temperature above the melting point of the surfactant; and
(c) cooling said final mixture to a temperature below the melting point of the surfactant to form an N-phosphonomethyl-N-carboxymethyl composition which is solid at ambient temperature, wherein said N-phosphonomethyl-N-carboxymethyl compound is dispersed throughout a matrix formed by said surfactant.

12. A method according to claim 11 wherein the N-phosphonomethyl-N-carboxymethyl compound is of the formula

and wherein M is independently selected from hydrogen and agriculturally acceptable salt-forming moieties.

13. A method according to claim 12 wherein one M is selected from an agriculturally acceptable salt-forming moiety and the remaining M's are hydrogen.

14. A method according to claim 11 wherein the N-phosphonomethyl-N-carboxymethyl compound is N,N-bis-(phosphonomethyl)glycine.

15. A method according to claim 12 wherein the N-phosphono-N-carboxymethyl compound is N-phosphonomethylglycine.

16. A method according to claim 13 wherein the N-phosphonomethyl-N-carboxymethyl compound is isopropylamine-N-phosphonomethylglycine.

17. A method according to claim 13 wherein the N-phosphonomethyl-N-carboxymethyl compound is trimethylsulfonium-N-phosphonomethylglycine.

18. A method according to claim 11 further comprising processing the solid, phytoactive composition into a particulate form.

19. A method according to claims 11, 12, 13, 14, 15, 16, 17 or 18 wherein the surfactant is nonionic.

20. A method according to claims 11, 12, 13, 14, 15, 16, 17 or 18 wherein the surfactant is an ethylene oxide or propylene oxide block copolymer.

21. A method according to claims 11, 12, 13, 14, 15, 16, 17 or 18 wherein the surfactant is a block copolymer of alkyl oxides having a function group

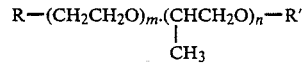

wherein R and R' are independently selected from hydrogen,

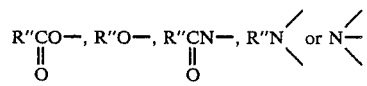

wherein R' is selected from an alkyl group having from about 8 to about 30 carbon atoms or alkylaryl groups, wherein the alkyl portion of the alkylaryl group ranges from about 8 to about 30 carbon atoms, and mixtures thereof, and wherein m ranges from about 20 to about 200, n ranges from about 0 to about 10, and m+n is equal to or greater than about 25.

22. A method according to claim 21 wherein substantially all the solvent is removed.

23. A method according to claim 21 wherein the ratio of N-phosphonomethyl-N-carboxymethyl compound to surfactant, by weight, is from about 10:1 to about 1:10.

24. A method according to claim 21 wherein the ratio of N-phosphonomethyl-N-carboxymethyl compound to surfactant, by weight, is from about 4:1 to about 1:2.

25. A composition according to claim 10 wherein the ratio of N-phosphonomethyl-N-carboxymethyl compound to surfactant, by weight, is from about 10:1 to about 1:10.

26. A composition according to claim 10 wherein the ratio of N-phosphonomethyl-N-carboxymethyl compound to surfactant, by weight, is from about 4:1 to about 1:2.

* * * * *